(12) United States Patent
Styrc (10) Patent No.: US 8,109,986 B2
(45) Date of Patent: Feb. 7, 2012

(54) DEVICE FOR INSERTING A RADIALLY EXPANDABLE IMPLANT, TREATMENT KIT AND ASSOCIATED INSERTION METHOD

(75) Inventor: Mikolaj Witold Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 806 days.

(21) Appl. No.: 12/076,628

(22) Filed: Mar. 20, 2008

(65) Prior Publication Data

US 2008/0234797 A1    Sep. 25, 2008

(30) Foreign Application Priority Data

Mar. 21, 2007    (FR) ...................................... 07 53959

(51) Int. Cl.
*A61F 2/06* (2006.01)
(52) U.S. Cl. ...... 623/1.12; 623/1.11; 623/1.1; 623/2.11; 623/2.1
(58) Field of Classification Search .................. 606/108, 606/109; 623/1.1, 1.12, 1.23, 1.24–1.26, 623/1.3, 1.31, 2.11, 902–908, 11.11
See application file for complete search history.

(56) References Cited

U.S. PATENT DOCUMENTS

| | | | |
|---|---|---|---|
| 5,464,449 A | 11/1995 | Ryan et al. | |
| 5,713,948 A | 2/1998 | Uflacker | |
| 5,776,186 A | 7/1998 | Uflacker | |
| 6,183,504 B1 * | 2/2001 | Inoue | 623/1.11 |
| 6,302,891 B1 * | 10/2001 | Nadal | 606/108 |
| 6,398,802 B1 | 6/2002 | Yee | |
| 6,517,550 B1 * | 2/2003 | Konya et al. | 606/113 |
| 6,533,811 B1 * | 3/2003 | Ryan et al. | 623/1.23 |
| 6,740,111 B1 * | 5/2004 | Lauterjung | 623/1.1 |
| 6,821,291 B2 * | 11/2004 | Bolea et al. | 623/1.11 |
| 6,984,244 B2 * | 1/2006 | Perez et al. | 623/1.23 |
| 2002/0029076 A1 | 3/2002 | Yee | |
| 2002/0038144 A1 | 3/2002 | Trout, III et al. | |
| 2004/0049256 A1 * | 3/2004 | Yee | 623/1.12 |
| 2005/0119722 A1 * | 6/2005 | Styrc et al. | 623/1.12 |
| 2007/0100427 A1 * | 5/2007 | Perouse | 623/1.11 |
| 2007/0233223 A1 * | 10/2007 | Styrc | 623/1.11 |
| 2009/0048656 A1 * | 2/2009 | Wen | 623/1.12 |
| 2010/0268322 A1 * | 10/2010 | Styrc et al. | 623/1.15 |

FOREIGN PATENT DOCUMENTS

| | | |
|---|---|---|
| FR | 2863160 | 6/2005 |
| WO | 95/01761 | 1/1995 |
| WO | 97/03624 | 2/1997 |
| WO | 00/78248 | 12/2000 |
| WO | 01/60285 | 8/2001 |
| WO | 2006/134258 | 12/2006 |

* cited by examiner

OTHER PUBLICATIONS

International Search Report issued Sep. 10, 2007 in the International (PCT) Application of which the present application is the U.S. National Stage.

*Primary Examiner* — Corrine M McDermott
*Assistant Examiner* — Todd J Scherbel
(74) *Attorney, Agent, or Firm* — Wenderoth, Lind & Ponack, L.L.P.

(57) ABSTRACT

A device includes a support defining at least one opening for retaining an implant situated in the vicinity of the distal end thereof, and at least one threadlike link for retaining the implant. The link includes a control portion engaged in the support and a tightening loop of the implant which projects outside the support through the retention opening. A component is provided for placing each tightening loop around the implant. The placement component includes a rigid member and at least one flexible cord integral with the member and engaged releasably around the tightening loop.

14 Claims, 5 Drawing Sheets

DEVICE FOR INSERTING A RADIALLY EXPANDABLE IMPLANT, TREATMENT KIT AND ASSOCIATED INSERTION METHOD

BACKGROUND OF THE INVENTION

The present invention relates to a device for inserting an implant that can expand radially between a contracted state and a dilated state, the device being of the type comprising: a hollow support defining at least one opening for retaining the implant situated in the vicinity of the distal end thereof; and at least one threadlike link for retaining the implant. The link includes a control portion engaged in the support and a tightening loop connected to the control portion and intended to encircle the implant, with the tightening loop projecting outside the support through the retention opening.

Such a device is applicable for insertion into a blood vessel of a tubular endoprosthesis, widely referred to by the term "stent", or of an endovalve comprising a tubular endoprosthesis and a valve fixed on the endoprosthesis.

A device of the above-mentioned type is disclosed in EP-A-0 707 462. An endoprosthesis is mounted coaxially on two hollow supports, which are capable of sliding in relation to each other. The endoprosthesis is held in the retracted state using threadlike links that encircle the ends thereof. The threadlike links are engaged respectively in the distal and proximal retention openings arranged respectively in one or the other of the supports.

To insert the endoprosthesis, the supports are moved by sliding relative to each other, so that the distance between the retention openings is reduced.

The reduction of this distance causes the threadlike links to loosen and consequently leads to the simultaneous deployment of both ends of the endoprosthesis.

Such a device is not entirely satisfactory. Indeed, given the complexity of the insertion device, loading of the endoprosthesis onto the device must be carried out in the factory during manufacture of the insertion device. Consequently, it is not possible for the surgeon to modify the size of the endoprosthesis mounted on the insertion device just before the operation, depending on the morphological characteristics of the patient. The surgeon must therefore provide, in the operating theatre, endoprostheses of varied dimensions to suit the morphology of the patient to be treated, which is expensive.

Moreover, if the endoprosthesis has a flexible valve, the valve must be kept in a physiological solution separate from the insertion device. It is therefore not possible to use such an insertion device with endovalves.

An object of the invention is therefore to obtain an insertion device comprising a support and at least one threadlike retention link forming a tightening loop of adjustable size, in which the expandable implant can easily be loaded onto the insertion device by the surgeon just before an operation.

SUMMARY OF THE INVENTION

Accordingly, the invention relates to a device of the above-mentioned type, in which the device comprises at least one tool for placing each tightening loop around the implant. The placement tool comprises a rigid member and at least one flexible cord integral with the member and engaged releasably round the tightening loop.

The insertion device according to the invention may comprise one or more of the following characteristics, taken in isolation or according to any technically possible combination(s):

each placement tool comprises at least two flexible cords engaged in two positions spaced around the tightening loop;

the member has one end defining at least one rounded shape or point, each cord being fixed on the member at a point spaced longitudinally relative to the rounded shape or point; and each cord defines a loop sliding freely along the tightening loop.

Another object of the invention is a treatment kit that comprises at least one implant that is radially expandable between a contracted state and a dilated state, and an insertion device as defined above. The treatment kit according to the invention may comprise the following characteristic: the implant comprises a tubular mesh comprising, for each threadlike link, at least one ring for guiding the link, the ring delimiting a passage of substantially complementary size of the member.

Another object of the invention is a method for loading an implant that is radially expandable between a contracted state and a dilated state on an insertion device as defined above, and the method includes the following stages:

expansion of the tightening loop outside the support by moving the placement tool away from the support;

engagement of the tightening loop around the implant;

contraction of the tightening loop towards the support; and release of each flexible cord relative to the tightening loop.

The method according to the invention may comprise one or more of the following characteristics, taken in isolation or according to any combination(s) that are technically possible.

The implant can comprise an endoprosthesis comprising a tubular framework, and the method can comprise a stage of passing the rigid member and each flexible cord through the tubular framework, before engaging the tightening loop around the endoprosthesis.

The tubular framework can define a ring for guiding the member, and the method can comprise the passage of the member and each flexible cord through the ring before engaging the loop around the endoprosthesis.

Another object of the invention is a placement tool for a device for inserting an implant that can expand radially between a contracted state and a dilated state. The placement tool comprises a rigid member and at least two flexible cords having one end integral with the member and one end free forming a loop intended to be engaged around a tightening loop of the insertion device.

BRIEF DESCRIPTION OF THE DRAWINGS

The invention will be better understood upon reading the description that follows, given solely by way of example, and made with reference to the accompanying drawings, in which.

DETAILED DESCRIPTION OF THE PREFERRED EMBODIMENT

Figure 1:
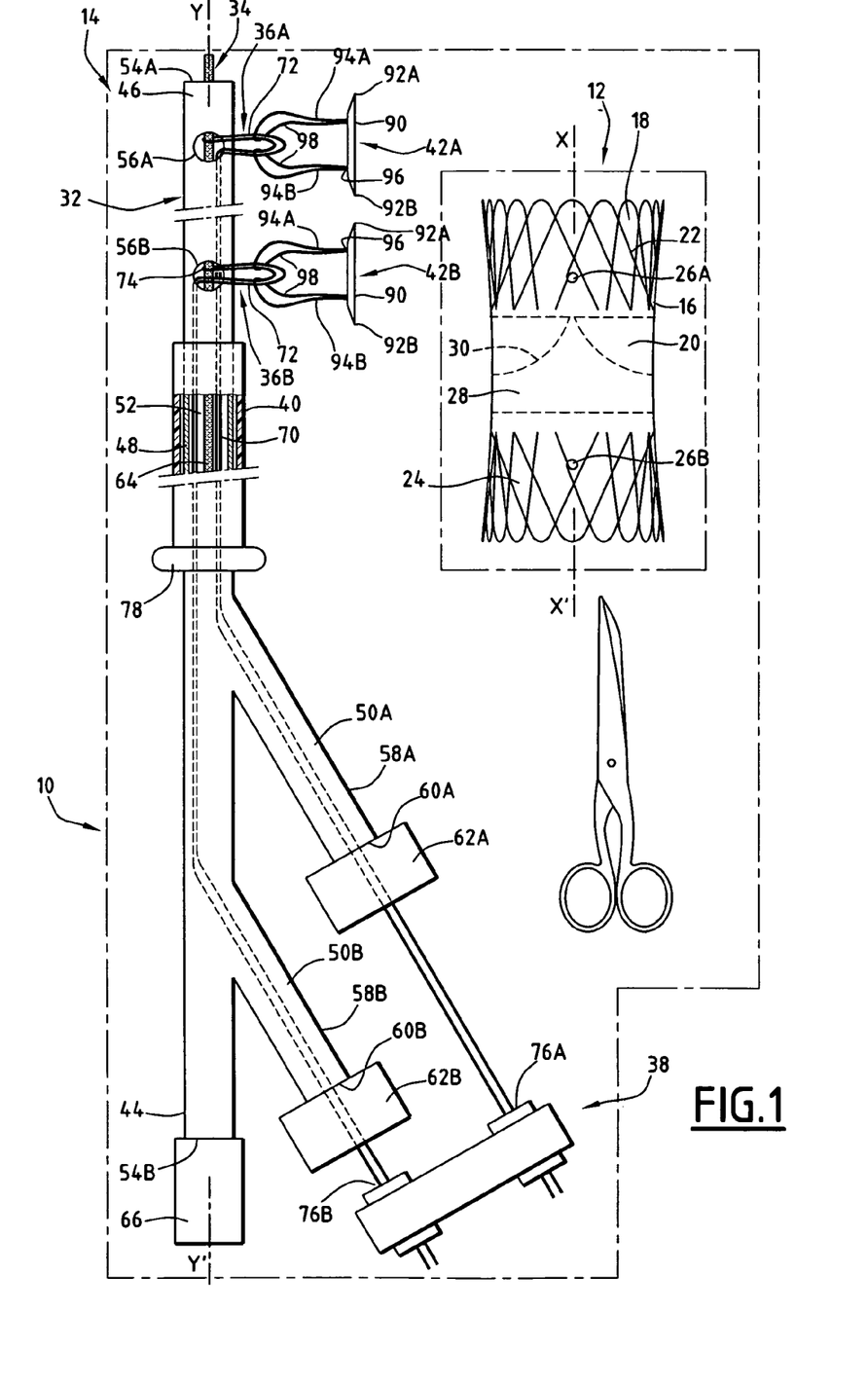
FIG. 1 is a view from above in partial section of a first treatment kit according to the invention.

FIG. 1 illustrates a first treatment kit 10 for a blood circulation conduit according to the invention. As illustrated in FIG. 1, the kit comprises a radially expandable implant 12, an insertion device 14 for an implant 12, and scissors.

In the example illustrated in FIG. 1, the implant 12 is an endovalve. The endovalve 12 is kept in a damp and sterile medium, such as physiological serum for example. It comprises a tubular endoprosthesis 16 delimiting an internal blood circulation conduit 18, and a valve 20 fixed on the endoprosthesis 16 inside the conduit 18.

The endoprosthesis 16 is formed by a framework consisting of a tubular mesh 22 which has the properties of a spring. The mesh 22 is obtained by weaving at least one thread made of stainless steel, a shape-memorizing alloy, or a polymer. In a variant, the mesh is obtained by laser-cutting a tube.

The mesh 22 comprises a plurality of threadlike segments 24 which intersect and delimit transverse lozenge-shaped openings. It also comprises a distal ring 26A and a proximal ring 26B for guiding the insertion device as described below.

The rings 26A, 26B are integral with the segments 24. They are situated respectively in the vicinity of a distal end and a proximal end of the mesh 22.

The mesh 22 of the endoprosthesis 16 can be deployed in the contracted state in which it has a small diameter, and in a dilated state, constituting its rest state, in which it has a large diameter.

In the example illustrated in FIG. 1, the mesh can be deployed spontaneously between its contracted state and its dilated state.

The valve 20 is for example produced from a valve of an animal such as a pig. In a variant, it is produced from natural tissue such as bovine or ovine pericardium, or from synthetic material.

Traditionally, the valve 20 comprises a tubular base 28, fixed on the mesh 22 and extended upwards by three flexible leaves 30 for closing the conduit 18.

The leaves 30 can be moved radially towards the axis X-X' of the conduit 18 between a closed position of the conduit 18, in which they substantially prevent the passage of blood through the conduit 18, and an open position of the conduit 18, in which they are substantially laid flat against the mesh 22 and they allow the blood to pass through the conduit 18.

The valve 20 is arranged axially on the mesh 22 between the guide rings 26A, 26B, at a distance from these rings.

As illustrated in FIG. 1, the insertion device 14 comprises a hollow support 32, a retention pin 34 engaged in the hollow support, threadlike links 36A, 36B for retaining and tightening the endovalve 12 against the support 32, and a control bar 38 for maneuvering the threadlike links 36A, 36B.

The insertion device 14 also comprises a sheath 40 for protecting the endovalve 12, mounted so as to slide coaxially on the support 32. According to the invention, the device 14 comprises, for each threadlike link 36A, 36B, a placement tool 42A, 42B connected to the threadlike link 36A, 36B.

The hollow support 32 extends between a proximal end 44 intended to be placed outside the human body to be accessible to the surgeon, and a distal end 46 intended to be implanted in the blood circulation conduit, in particular by the endoluminal route.

The support 32 comprises a hollow tube 48 with a central axis Y-Y', and for each threadlike link 36A, 36B, a lateral branch 50A, 50B opening into the hollow tube 48, in the vicinity of the proximal end 44.

The hollow tube 48 delimits internally a central passage 52 of axis Y-Y', which opens axially at the distal 46 and proximal 44 ends of the tube 48 through respective axial openings 54A, 54B. The hollow tube 48 also delimits, for each threadlike retention link 36A, 36B, a transverse retention opening for the endovalve 12, which opens in the vicinity of the distal end 46 and in which the link 36A, 36B is engaged.

In the example illustrated in FIG. 1, the insertion device 14 comprises two threadlike links 36A, 36B and two corresponding transverse retention openings 56A, 56B.

The transverse openings 56A, 56B are spaced longitudinally along the axis Y-Y'. The distance separating said openings is substantially equal to the distance separating the distal ring 26A from the proximal ring 26B when the mesh 22 of the endovalve 12 occupies the contracted state thereof against the support 32.

The branches 50A, 50B project transversely relative to the hollow tube 48 in the vicinity of the proximal end 44. They have respective internal passages 58A, 58B connecting the central passage 52 to respective outer openings 60A, 60B.

Locking caps 62A, 62B are mounted on the free ends of the branches 50A, 50B in the region of the openings 60A, 60B and selectively lock in position or release the respective threadlike links 36A, 36B.

The retention pin 34 comprises a retention rod 64 arranged axially in the passage 52 and a fixing cap 66 screwed to the proximal end 44 of the hollow tube 48.

The shaft 64 can be moved axially in the conduit, between a distal fixing position, in which it extends opposite each transverse retention opening 56A, 56B, an intermediate position in which it extends opposite the proximal retention opening 56B, and at a distance from the distal retention opening 56A towards the proximal end 44, and a proximal released position in which it extends at a distance from the openings 56A, 56B.

In the example illustrated in FIG. 1, each threadlike link 36A, 36B is formed by two parallel strands, folded in a loop at the distal end thereof.

Each threadlike link 36A, 36B thus comprises successively a control portion 70 connecting the control bar 38 to a retention opening 56A, 56B through the hollow support 32, a loop 72 for retaining and tightening the endovalve 12, which projects outside the retention opening 56A, 56B, and an end loop 74 engaged releasably around the retention rod 64.

Each control portion 70 is fixed at a proximal end 76A, 76B to the control bar 38. The ends 76A, 76B are thus fixed on either side of the control bar 38.

Each control portion 70 extends successively through a respective control cap 62A, 62B, in an inner passage 58A, 58B, in the central passage 52 and inside the hollow tube 48 as far as a retention opening 56A, 56B.

The retention loop 72 is connected to the control portion 70. It extends outside the retention opening 56A, 56B.

As is shown below, the loop 72 is of a variable active length which is adjusted by moving the control bar 38.

The loop 72 is integral at one end with the control portion 70 and at the other end with the loop 74 engaged on the retention rod 64.

The active length of the tightening loop 72 is variable. Thus, when the end 76A, 76B of the control portion 70 is close to the stopper 62A, 62B, the length of the control section 70 is reduced and the active length of the tightening loop 72 is increased. Conversely, when the control bar 38 is moved so that the end 76A moves away from the stoppers 62A, 62B, the active length of the tightening loop 72 is reduced.

Figure 6:
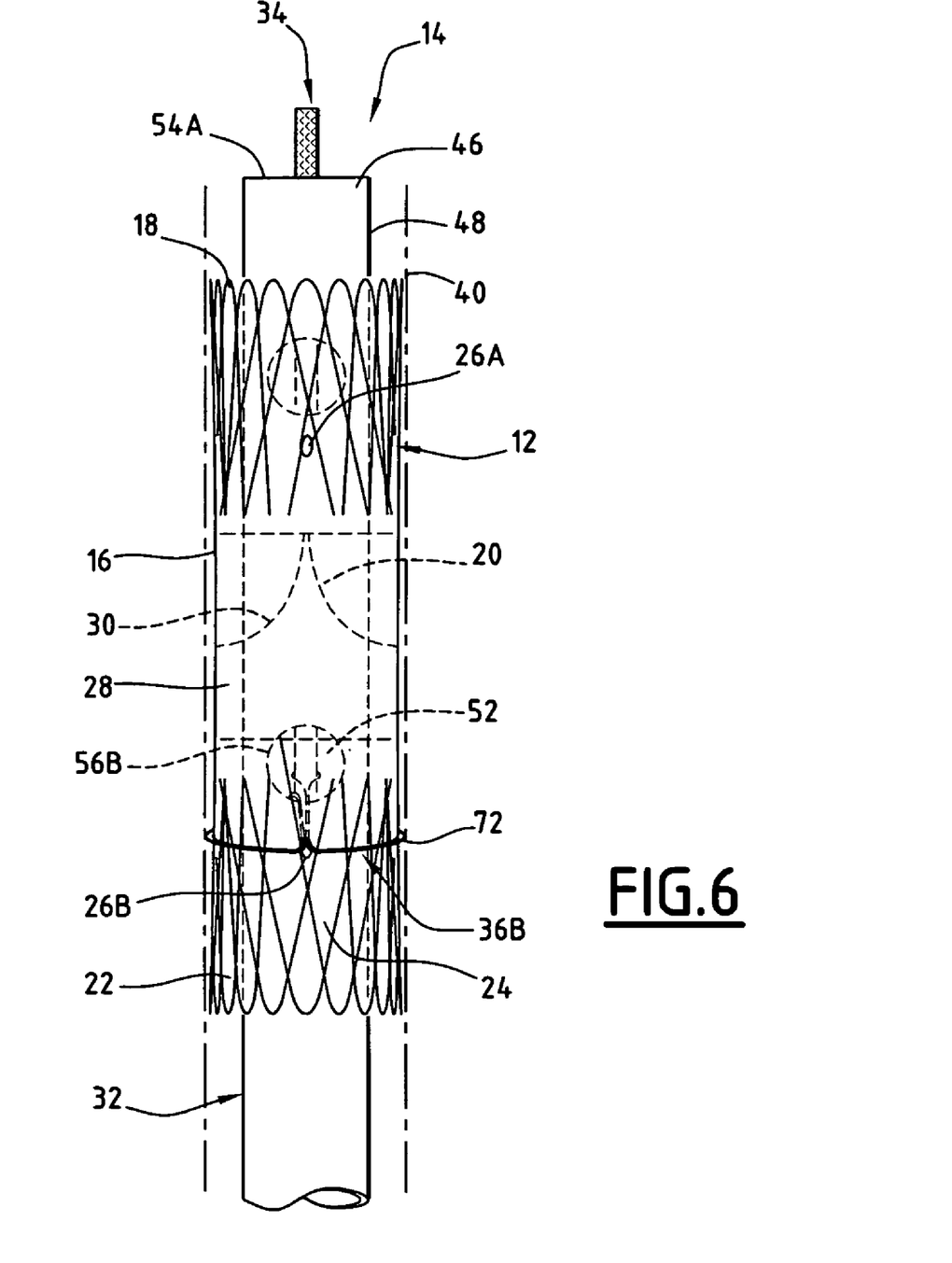
FIG. 6 is a view similar to FIG. 3 of a fourth stage of the method.

As illustrated in FIG. 6, the tightening loops 72 are intended to encircle the endovalve 12 at the ends thereof when the endovalve 12 is mounted on the insertion device 14. The loops 72 thus, with their active length, control the radial expansion of the endovalve 12 when it is mounted coaxially around the support 32.

The protection sheath 40 is mounted so as to slide along the axis Y-Y' on the hollow support 32. It can be moved on the support 32 by means of proximal control lugs 78, between a withdrawn position in which it is placed at a distance from the retention openings 56A, 56B, and an advanced position in which it covers the retention openings 56A, 56B.

Figure 2:
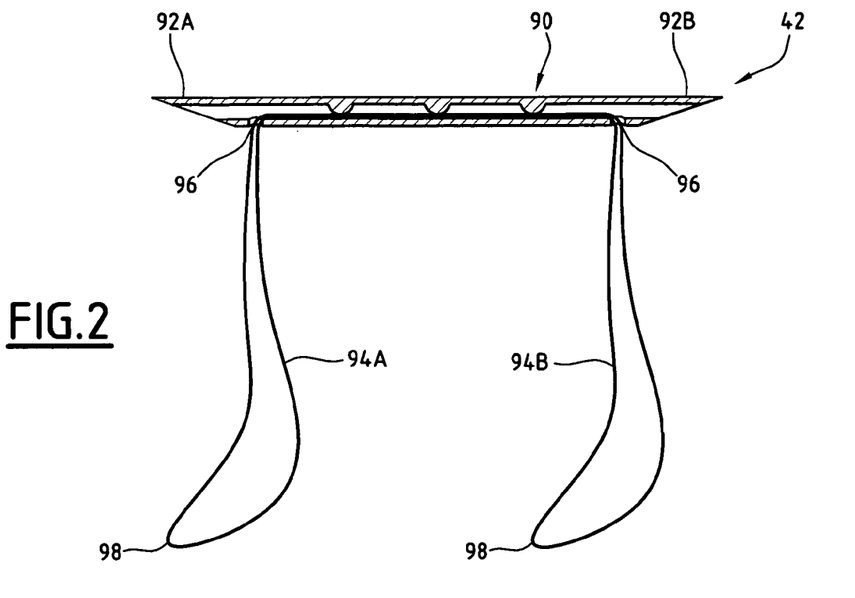
FIG. 2 is a view of a tool for placing a tightening loop of the kit of FIG. 1.

According to the invention and as illustrated in FIG. 2, each placement tool 42A, 42B comprises a rigid member 90 extending longitudinally between two ends 92A, 92B, and two flexible actuating cords 94A, 94B intended to be engaged around a tightening loop 72.

As illustrated in FIG. 2, the member 90 has a length, taken between the ends 92A, 92B thereof, of between 1 centimeter and a plurality of centimeters, for example. It also has a diameter of between 0.2 millimeters and a plurality of millimeters, for example.

The member 90 is cut in the form of a point or in a rounded shape at each of the ends 92A, 92B thereof. The acute angle formed by the point of the member facilitates the threading of the member 90 into a guide ring 26A, 26B.

The outer diameter of the member 90 corresponds substantially to the inner diameter of a guide ring 26A, 26B.

The cords 94A, 94B are fixed on either side of the member 90.

Each cord 94A, 94B has an end 96 fixed to the member 90, at a distance longitudinally from the bevelled point defined at each end 92A, 92B, and a free end 98 forming a loop.

In the example illustrated in FIG. 2, each flexible cord 94A is formed by two strands connected in a loop in the region of the free end 98 and in the region of the fixed end 96.

The strands constituting the cord 94A and the cord 94B are for example connected to each other through the member and fixed on the member by pressing of the member.

During manufacture of the device 14, each free end 98 is engaged freely around the tightening loop 72 of a threadlike link 56A, 56B. In other words, the cord 94A, 94B of each respective free end 98 extends through a respective loop 72 of the threadlike link so that each free end 98 encircles and engages the respective threadlike link 56A, 56B forming the respective loop 72 so that the respective free end 98 engages the respective loop 72. Each free end 98 can therefore be slid along the loop 72. The free ends 98 of the respective cords 94A, 94B are spaced along the tightening loop 72.

The cords 94A, 94B can be moved relative to the member 90 between a near position, in which the free ends 98 thereof are placed in the vicinity of each other and in which they define with the member 90 a triangle, and a separated position, illustrated in FIG. 4, in which the free ends 98 thereof have been separated at a distance from each other for the expansion of the tightening loop 72, as described below.

The scissors 16 are suitable for cutting the flexible cords 94A, 94B of the placement components 42 to release them from the loop 72.

The method of loading the endovalve 12 on the insertion device 14 is described below.

Initially, the endovalve 12 is kept sterile in a moist medium, such as a solution of physiological serum, for example. The mesh 22 of the endoprosthesis 16 is in the dilated rest state, which keeps the valve 20 in a rest configuration, minimizing the stresses that could be applied to it.

Similarly, the insertion device 14 is kept in a sterile sachet. The locking caps 62A, 62B are released to allow movement of the control portions 70. In addition, the tightening loops 72 are withdrawn outside the retention openings 56A, 56B. A placement tool 42A, 42B is engaged on each tightening loop 72.

The cords 94A, 94B of the tools 42A, 42B are thus engaged around strands forming the tightening loop 72A, 72B. In addition, the sheath 40 is in the withdrawn position to facilitate access to the retention openings 56A, 56B.

The retention rod 64 of the retention pin 34 is in the distal position and the loops 74 of the threadlike links 36A, 36B are engaged around the retention pin 34.

Just before the introduction of the endovalve 12 into a patient, during an operation, the surgeon puts the endovalve 12 in place on the insertion device 14.

Accordingly, he inserts the endovalve 12 coaxially at the distal end 46 of the support 32 by introducing the support 32 into the blood circulation conduit 18 through the leaves of the valve 20.

Figure 3:
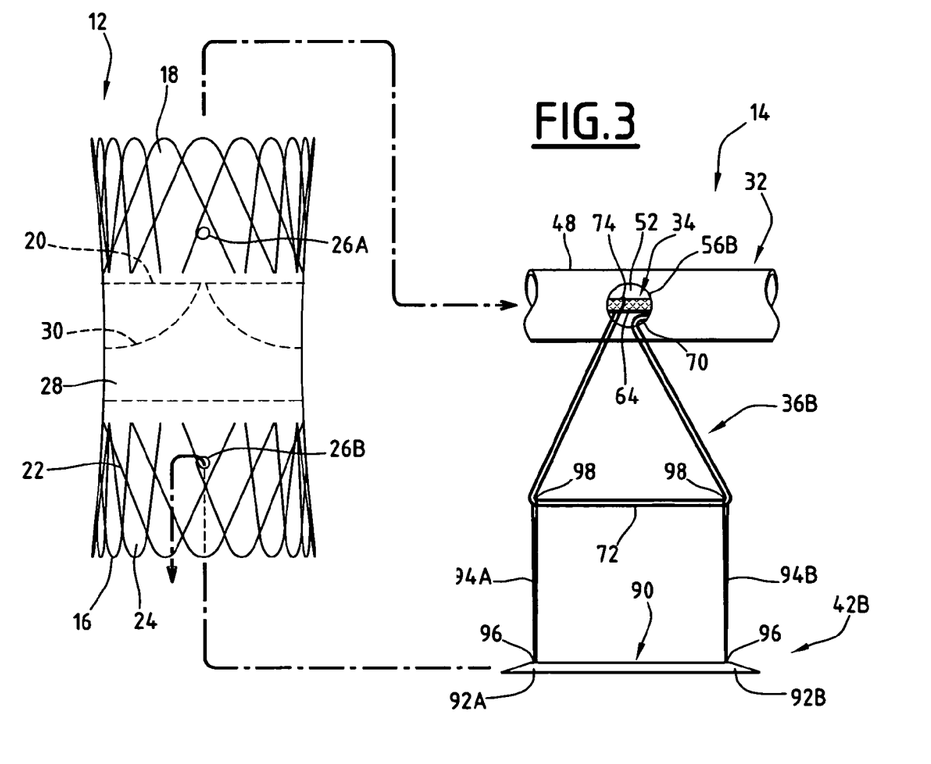
FIG. 3 is a partial diagrammatic perspective view of a first stage of the method of placing an implant on the insertion device of the kit of FIG. 1.

Then, he fits the proximal tightening loop 72 around the endoprosthesis 16 of the endovalve 12. Accordingly, and as illustrated in FIG. 3, he applies traction to the rigid member 90 of the placement tool 42B to introduce the rigid member 90 into the inside of the conduit 18. Then, he engages a bevelled or rounded point situated at the end 92A of the member 90 in the proximal ring 26B and successively withdraws the member 90, the cords 94A, 94B and the tightening loop 72 from inside the conduit 18 towards the outside of said conduit 18 through the mesh 22 of the endoprosthesis 16.

Figure 4:
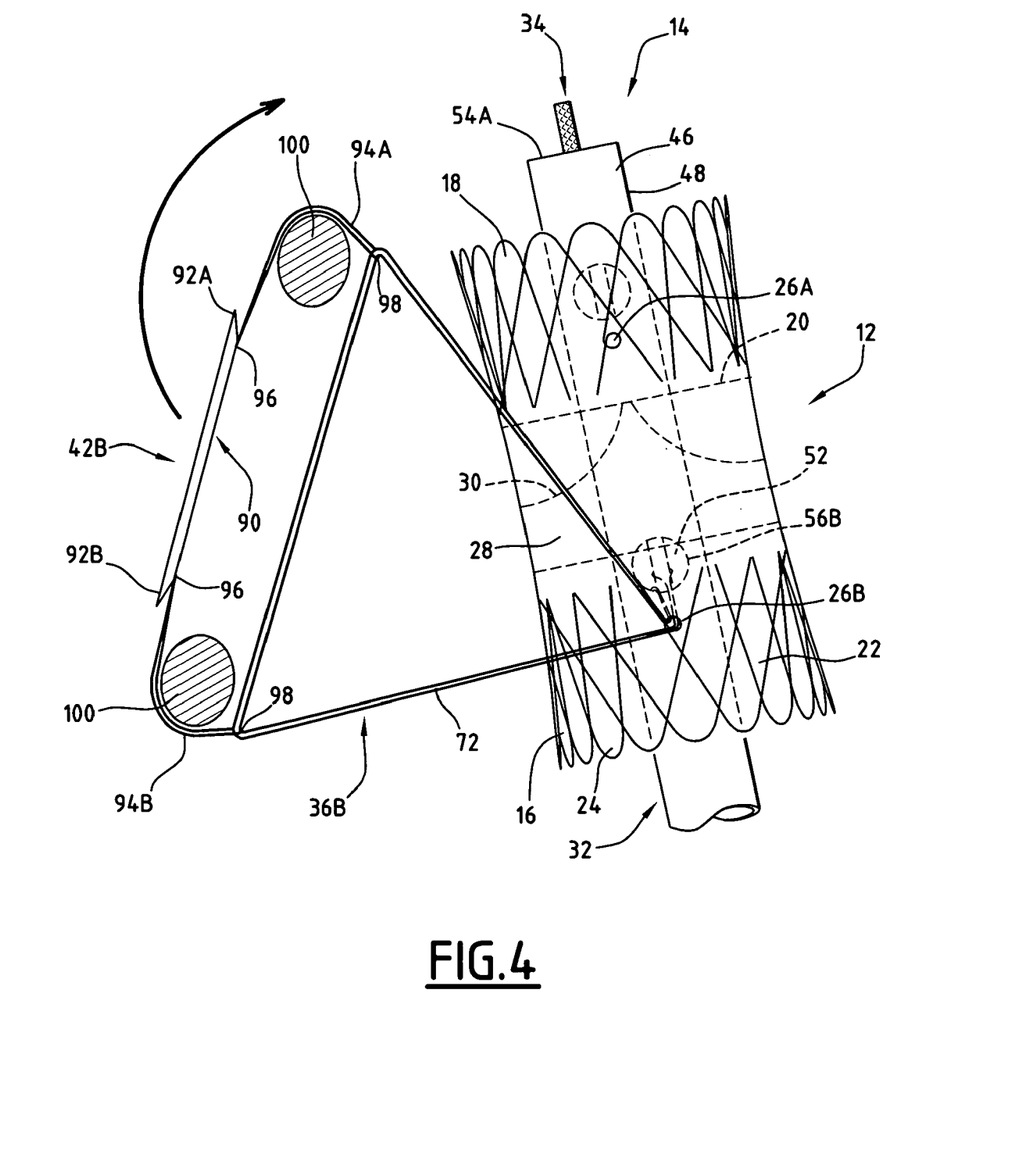
FIG. 4 is a view similar to FIG. 3 of a second stage of the method.

As illustrated in FIG. 4, the ends of the tightening loop 72 are then held in the guide ring 26B.

Then, taking the member 90, the surgeon separates the cords 94A, 94B at a distance from each other by means of his fingers 100 to move the free ends 98 of the cords 94A, 94B away from each other.

This action causes the tightening loop 72 to expand outside the support 32 and leads to an increase in the active length thereof as illustrated in FIG. 4. This expansion continues, until the surface delimited internally by the tightening loop 72 is greater than the maximum cross-section of the endoprosthesis 16.

Figure 5:
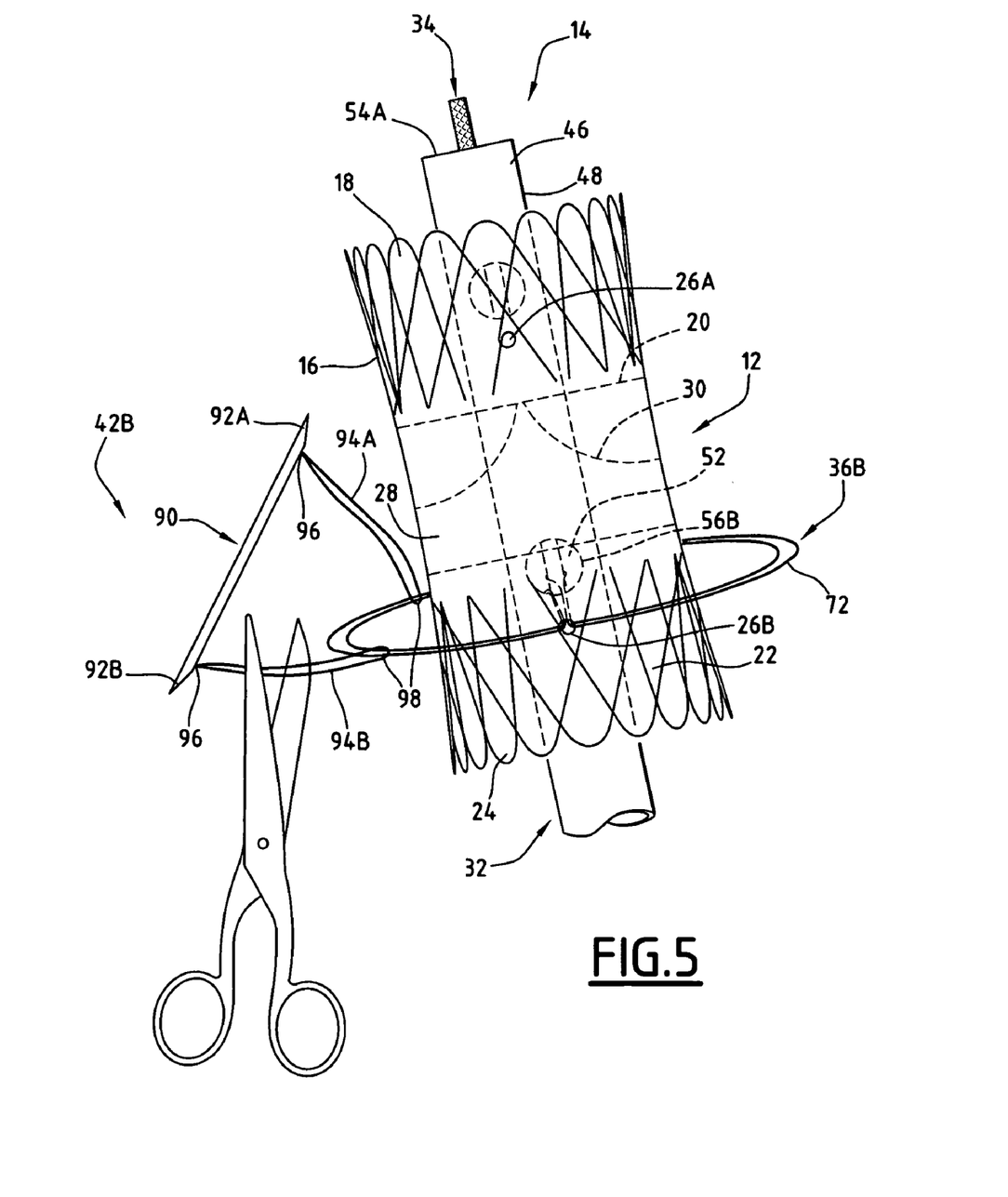
FIG. 5 is a view similar to FIG. 3 of a third stage of the method.

Once this has been done, he engages the tightening loop 72 coaxially around the outer surface of the endoprosthesis 16, pivoting the loop 72 about an axis perpendicular to the axis X-X', using the placement tool 42B. He thus causes the endovalve 12 and the support 32 to penetrate into the inside of the loop 72. As illustrated in FIG. 5, the tightening loop 72 then extends substantially perpendicular to the axis Y-Y' of the support around the endoprosthesis 16. It then encircles the endoprosthesis 16 in the vicinity of the proximal end thereof.

Next, the surgeon applies fraction to the end 76B of the control section by means of the control bar 38 by moving the end 76B away from the stopper 62B. During the traction, the active length of the tightening loop 72 reduces, which causes the radial contraction of the proximal end of the endoprosthesis 16 towards the support 32.

He then engages the distal tightening loop 72 in a similar way to that described for the proximal loop, by engagement of the member 90 and cords 94A, 94B through the distal guide ring 26A. Next, he tightens the distal tightening loop 72 by means of the control bar 38 until the distal end of the endoprosthesis 16 contracts radially against the support 34. The endoprosthesis 16 is then in the contracted state.

When he considers that the insertion device 14 is operating correctly, he uses the scissors 16 to cut the cords 94A, 94B and thus release the placement tools 42A, 42B from the tightening loops 72.

Once this has been done, he moves the sheath 40 towards the distal end 46 of the support 32 to cover the endoprosthesis 16 in the contracted state thereof and introduces it into the human body.

The procedure for implanting the endovalve 12 in the human body is then carried out, as described in application FR-A-2 863 160 of the Applicant.

Accordingly, the insertion device 14, on which the endovalve 12 is mounted, is introduced up to the point of implantation by endoluminal means, by sliding on a surgical guide, then the sheath 40 is withdrawn towards the proximal end 44. The endovalve 12 is then inserted by successive or simultaneous deployment of the tightening loops 72 under the action of the control bar 38. When the insertion is satisfactory, the retention pin 34 is withdrawn to allow the retention rod 64 thereof to pass to the release position. The threadlike retention links 36A, 36B are then withdrawn outside the human body by traction on the control bar 38, and the support 32 is withdrawn.

With the help of the invention that has just been described, it is thus possible to have an insertion device 14 where an endoprosthesis 16 or endovalve 12 can be easily loaded onto the device by the surgeon just before the operation. The presence of a rigid member 90 facilitates the engagement of the tightening loops 72 through the endoprosthesis 16 or endovalve 12 and around it. The presence of the flexible cords 94A, 94B allows the active length of said loops 72 to be made to expand in a simple manner.

In a variant, the mesh 22 does not have a guide ring. In this case, the end of the member 90 is introduced through a closed link, defined between the threadlike segments 24 of the mesh 22, when mounting the tightening loops 72.

In another variant (not illustrated), the insertion device 14 comprises a single threadlike link forming at least one tightening loop encircling the endoprosthesis 16, after it has been loaded on the device 14.

In a variant, the endoprosthesis 16 is mounted laterally along the support 32 when it is loaded on the device 14. Thus, the outer surface of the endoprosthesis 16, and not its inner surface delimiting the conduit 18, is kept applied against the support 32 by the links 36A, 36B.

In another variant, each link 36A, 36B encircles the endoprosthesis 16 at a point situated at a distance from the ends of the endoprosthesis 16 over the length thereof.

What is claimed is:

1. An insertion device for inserting an implant, the implant being radially expandable between a contracted state and a dilated state in a blood circulation conduit, said device comprising:
   a hollow support having a distal end, a proximal end, and a retention opening situated in a vicinity of said distal end;
   a threadlike link for retaining the implant, said threadlike link including a control portion located in said hollow support and a tightening loop portion connected to said control portion and configured to encircle the implant, said tightening loop portion projecting outside said hollow support through said retention opening; and
   a placement tool for placing said tightening loop portion around the implant, said placement tool including:
   a rigid member;
   a first flexible cord integral with said rigid member, said flexible cord extending through said tightening loop portion of said threadlike link so as to form a loop encircling said threadlike link to thereby engage said flexible cord with said tightening loop portion; and
   a second flexible cord integral with said rigid member and extending through said tightening loop portion of said threadlike link so as to form a loop encircling said threadlike link to thereby engage said flexible cord with said tightening loop portion, said first flexible cord and said second flexible cord being located along said rigid member so as to engage said tightening loop portion at two positions spaced apart around said tightening loop portion.

2. The device of claim 1, wherein said rigid member has an end with a rounded shape, said first flexible cord being fixed on said rigid member at a position spaced longitudinally relative to said end with said rounded shape.

3. The device of claim 1, wherein said rigid member has an end with a pointed shape forming an acute angle, said first flexible cord being fixed on said rigid member at a position spaced longitudinally relative to said end with said pointed shape.

4. The device of claim 1, wherein said first flexible cord forms a loop encircling said threadlike link and configured to slide freely along said tightening loop portion.

5. The device of claim 1, wherein said rigid member has a pair of opposite ends, each of said opposite ends having a pointed shape forming an acute angle; and
   wherein each of said first flexible cord and said second flexible cord is located at a respective one of said opposite ends of said rigid member.

6. The device of claim 1, wherein said retention opening comprises a first retention opening, said hollow support further having a second retention opening spaced apart from said first retention opening along a longitudinal axis of said hollow support.

7. A treatment kit for treating a blood circulation conduit, said kit comprising:
   an implant radially expandable between a contracted state and a dilated state; and
   an insertion device for inserting said implant into the blood circulation conduit, said device comprising:
   a hollow support having a distal end, a proximal end, and a retention opening situated in a vicinity of said distal end;
   a threadlike link for retaining said implant, said threadlike link including a control portion located in said hollow support and a tightening loop portion connected to said control portion and configured to encircle said implant, said tightening loop portion projecting outside said hollow support through said retention opening; and
   a placement tool for placing said tightening loop portion around said implant, said placement tool including:
   a rigid member;
   a first flexible cord integral with said rigid member, said flexible cord extending through said tightening loop portion of said threadlike link so as to form a loop encircling said threadlike link to thereby engage said flexible cord with said tightening loop portion; and
   a second flexible cord integral with said rigid member and extending through said tightening loop portion of said threadlike link so as to form a loop encircling said threadlike link to thereby engage said flexible cord with said tightening loop portion, said first flexible cord and said second flexible cord being located along said rigid member so as to engage said tightening loop portion at two positions spaced apart around said tightening loop portion.

8. The kit of claim 7, wherein said implant comprises a tubular mesh including a ring for guiding said tightening loop portion of said threadlike link, said ring defining a passage having a size corresponding to a size of said rigid member of said placement tool.

9. The kit of claim 7, wherein said rigid member has an end with a rounded shape, said first flexible cord being fixed on said rigid member at a position spaced longitudinally relative to said end with said rounded shape.

10. The kit of claim 7, wherein said rigid member has an end with a pointed shape forming an acute angle, said first flexible cord being fixed on said rigid member at a position spaced longitudinally relative to said end with said pointed shape.

11. The kit of claim 7, wherein said first flexible cord forms a loop encircling said threadlike link and configured to slide freely along said tightening loop portion.

12. The kit of claim 7, wherein said rigid member has a pair of opposite ends, each of said opposite ends having a pointed shape forming an acute angle; and
   wherein each of said first flexible cord and said second flexible cord being located at a respective one of said opposite ends of said rigid member.

13. The kit of claim 7, wherein said retention opening comprises a first retention opening, said hollow support further having a second retention opening spaced apart from said first retention opening along a longitudinal axis of said hollow support.

14. An insertion device for inserting an implant, the implant being radially expandable between a contracted state and a dilated state in a blood circulation conduit, said device comprising:

a hollow support having a distal end, a proximal end, and a retention opening situated in a vicinity of said distal end;
a threadlike link for retaining the implant, said threadlike link including a control portion located in said hollow support and a tightening loop portion connected to said control portion and configured to encircle the implant, said tightening loop portion projecting outside said hollow support through said retention opening; and
a placement tool for placing said tightening loop portion around the implant, said placement tool including:
   a rigid member having a pair of opposite ends, each of said opposite ends having a pointed shape forming an acute angle;
   a first flexible cord integral with said rigid member, said flexible cord extending through said tightening loop portion of said threadlike link so as to form a loop encircling said threadlike link to thereby engage said flexible cord with said tightening loop portion; and
   a second flexible cord integral with said rigid member and extending through said tightening loop portion of said threadlike link so as to form a loop encircling said threadlike link to thereby engage said flexible cord with said tightening loop portion, each of said first flexible cord and said second flexible cord being located at a respective one of said opposite ends of said rigid member.

\* \* \* \* \*